United States Patent [19]

Stockel

[11] Patent Number: 4,891,423

[45] Date of Patent: Jan. 2, 1990

[54] POLYMERIC BIGUANIDES

[76] Inventor: Richard F. Stockel, 475 Rolling Hills Rd., Bridgewater, N.J. 08807

[21] Appl. No.: 325,872

[22] Filed: Mar. 20, 1989

[51] Int. Cl.$^4$ .............................................. C08G 73/00
[52] U.S. Cl. ................................... 528/422; 523/122; 523/169; 524/612
[58] Field of Search ................ 528/422; 523/122, 169; 524/612

[56] References Cited

U.S. PATENT DOCUMENTS

| 4,403,078 | 9/1983 | McCoy et al. | 528/111 |
| 4,537,746 | 2/1985 | Ogunblyl et al. | 422/28 |

FOREIGN PATENT DOCUMENTS

| 702268 | 1/1954 | United Kingdom | 2/3 |
| 1152243 | 5/1969 | United Kingdom | 8/33 |
| 1432345 | 4/1976 | United Kingdom | 31/785 |
| 1531717 | 11/1978 | United Kingdom | 8/73 |

OTHER PUBLICATIONS

Texaco Chemical Co. brochure: "The Jeffamine® Polyoxyalkyleneamines", 1987.

Primary Examiner—Harold D. Anderson
Assistant Examiner—T. Mosley
Attorney, Agent, or Firm—Jack Matalon

[57] ABSTRACT

Linear, polymeric polyoxyalkylenediamine biguanide or water soluble salt thereof. The biguanide is useful as a biocide in bactericidal and fungicidal compositions and is especially useful as the active ingredient in ophthalmic compositions.

16 Claims, No Drawings

POLYMERIC BIGUANIDES

BACKGROUND

This invention relates to linear polyoxyalkylenediamine biguanides and water soluble salts thereof as well as to fungicidal or bacterial compositions and to ophthalmic or contact lens disinfecting compositions containing such biguanides or such salts thereof as the active ingredient therefor.

Bis-guanides and polymeric biguanides having structures differing from those of the present invention are known in the prior art. Such prior art biguanides are stated to have antibacterial and antifungal properties. See, for example, U.K. patent Nos. 702,268; 1,432,345; and 1,531,717. Other types of biguanides such as polyhexamethylene biguanide salts are known, and are stated to be useful as preservatives for cosmetics—see PCT Application WO86/02001, while yet other types of biguanides such as the polyether types and the polyoxyalkylenediamine types are stated to be useful as surfactants and epoxy resin curing agents—see U.S. Pat. Nos. 4,558,159 and 4,403,078.

There are several important advantages of the biguanides (and their water-soluble salts) of the present invention over the prior art biguanides. The unique structure of the present invention biguanides, particularly the alkylene oxide units, e.g. $-(CH_2CH_2-O)-$ and $-(CH_2-CHCH_3-O)-$, can be controlled to provide the desired hydrophilic-lipophilic balance ("HLB") in order to achieve maximum penetration of the cellular structure of the pathogenic organism. The degree of penetration, in turn, is determined by specific primary (e.g. ionic, covalent) interactions between the biguanide and the cell, as well as secondary (e.g. hydrogen bonding, hydrophobic) interactions as well as miscellaneous interactions such as van der Wall and dipole interactions.

Another outstanding property of the present invention is the unique ability of the biguanides to reduce the interfacial surface tension between the biocidal composition and cell and to thus permit improved adsorption on the surface of the cell. Moreover, the unique structure of the present biguanides suggests that they will be less sensitive to any organic matter suspended in aqueous solutions, i.e. less interaction, and therefore more efficacious when foreign matter is present.

When employed in ophthalmic saline solutions, the unique biguanides would be expected to overcome a problem common to prior art ophthalmic saline solutions. That is, ophthalmic solutions containing the biguanides of the present invention are expected to be less likely to adhere to contact lenses when they are washed with such saline solutions because the unique biguanides have significantly higher water solubilities and form stronger hydrogen bonding with water. That is, such biguanides solvate (i.e. interact with water) more readily than prior art biguanides having somewhat similar structures.

DETAILS OF THE PRESENT INVENTION

The present invention broadly comprises a linear, polymeric polyoxyalkylenediamine biguanide or water-soluble salt thereof which in the form of its free base comprises recurring units of the general formula

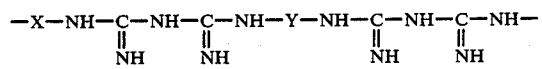

wherein X is a polyoxyalkylene radical and Y is a polymethylene radical of 2 to 18 carbon atoms or is the same as X. Preferably Y is a polymethylene radical of 5 to 15 carbon atoms.

The preferred choice of X in the above formula is a polyoxyalkylene radical derived from the amines selected from the group consisting of:

(a) amine-terminated polypropylene glycols having the structure:

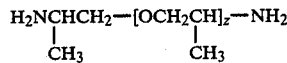

wherein z is an integer having a value of 2 to about 68;

(b) polyether diaines having the structure:

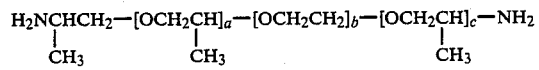

wherein b has a value of about 8.5 to about 131.5 and the value of a+c is about 2.5;

(c) bis-hydroxypropyl aminopolypropylene glycols having the structure:

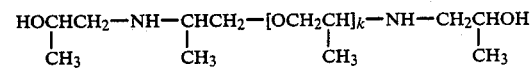

wherein k has a value of about 2.6;

(d) urea condensates of amine-terminated polypropylene glycols having the structure:

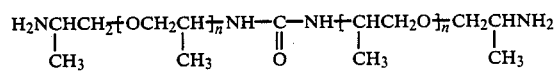

wherein n has a value of about 2.6; and (e) amine-terminated ethylene glycols having the structure:

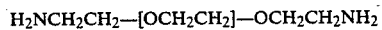

wherein m is an integer having a value of 1 to 3; and (f) amine-terminated polypropylene glycols having the structure:

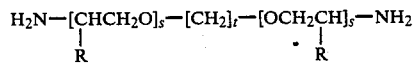

wherein s has a value of about 1 to about 10, t has a value of about 2 to about 8, and R is hydrogen or methyl.

The amine-terminated ethylene glycols shown in (e) above are the particularly preferred choices as the sources of the polyoxyalkylene radicals.

Also within the scope of the present invention are water soluble salts of the biguanides. Suitable examples of such salts are chlorides, bromides, iodides, acetates, citrates, glycolates, gluconates, sulphates, tartarates, phosphates, stearates, behenates, adipates, benzoates, phthalates, etc. Preferred salts are the gluconates. For the purposes of this invention, it should be understood that whenever the term "biguanide" is referred to, the aforementioned salts or the free base is intended.

The polymeric biguanides of the present invention find application as biocides, i.e. bactericides and fungicides for a wide variety of applications. The biguanides may be mixed with carriers which in turn may be either liquid or solid diluents and in the case of a water diluent, wetting agents, dispersing agents, emulsifying agents (anionic, cationic, non-ionic) may be added.

When combined with solid diluents, the compositions are useful as fungicides for agricultural purposes. Suitable solid carriers include kaolin, bentonite, kieselguhr, dolomite, calcium carbonate, talc, gypsum, diatomaceous earth, fuller's earth and the like.

One of the principal biocidal uses of the present invention is for ophthalmic compositions. The term "ophthalmic compositions" as employed herein is intended to encompass a variety of applications for contact lens of all types (e.g. hard, soft, semi-permeable, extended wear, etc.). Such applications include incorporation of the polymeric biguanides in, e.g. wetting solutions, enzyme cleaners, sterile saline solutions, preservatives for ophthalmological preparations, disinfectant solutions, etc.

Preferably the biguanides of the present invention are utilized in the form of aqueous emulsions or solutions, such as when employed as disinfectants or preservatives for contact lens. In the aqueous form, the compositions may be conveniently prepared in the form of concentrates. Such concentrates may contain 4-80%, preferably 10-30% of active ingredient. For contact lens purposes, the concentrate is diluted (e.g. with distilled water, saline, etc.) such that the final concentration of the biguanide employed in contact with the contact lenses is in the range of 0.001 to 0.1% by weight, based on the weight of the total composition.

When the biguanide in aqueous solution is to be used for ophthalmic purposes, the solution is preferably isotonic or substantially isotonic with tear fluid. Preferably, the aqueous solution will have a pH of 5.0-8.0, preferably 6.5-7.5. If desired, the composition may be buffered (with e.g. boric acid, sodium borate, potassium tetraborate, potassium metaborate, etc.) to maintain the pH in the desired range. The ophthalmic solution may also include one or more of the following ingredients: additional bactericides, e.g. thimerosal benzalkonium chloride, phenyl mercuric salts and the like; thickening agents, e.g. polyvinyl alcohol, carboxymethylcellulose, hydroxyethylcellulose and the like; nonionic surfactants such as polyethylene glycol esters of fatty acids, e.g. coconut, polysorbate, surfactants sold under the registered trademarks "Tween" (ICI Americas Inc.); "Tetronic" (BASF Wyandotte); "Pluronic" (BASF Wyandotte) and the like.

If desired, ophthalmic drugs may be added to the compositions, in which case the biguanide acts as a preservative for the drug solution. Suitable ophthalmic drugs include myotic drugs, e.g. pilocarpine; mydriatic drugs; anti-infective gents, e.g. chloramphenicol; and anti-inflammatory agents, e.g. steroids.

The biguanides of the present invention are readily prepared by reacting bisdicyandiamide types of compounds with polyoxyalkylene diamines, e.g. polyoxypropylenediamine, polyoxyethylenediamine, polyoxyethylene-propylenediamine block copolymers. The resultant linear, polymeric biguanides will have varying degrees of water solubility depending primarily on the number of oxyalkylene units in the final product.

The biscyandiamides employed as a starting material are well known and can be of several types. For example, they may have the general structure:

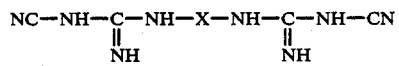

wherein X may be a $C_2$-$C_{12}$ polymethylene radical or a divalent radical which may be symmetrical aliphatic, aromatic, aliphatic aromatic, heterocyclic, phenylene-Z-phenylene wherein Z may be —S—, —SO—, —$SO_2$—, —S—S—, —$CH_2$—, —NH—, etc. as more fully described in British patent Nos. 1,531,717 and 1,167,249.

The other reactants, i.e. the polyoxyalkylenediamines are well known and are available from Texaco Chemical Co. under the registered trademark Jeffamines. Examples of such diamines include:

(a) amine-terminated polypropylene glycols having the structure:

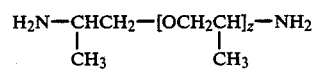

wherein z is an integer having a value of 2 to about 68;

(b) polyether diamines having the structure:

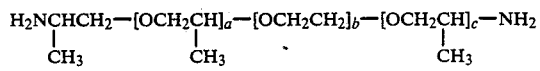

wherein b has a value of about 8.5 to about 131.5 and the value of a+c is about 2.5;

(c) bis-hydroxypropyl aminopolypropylene glycols having the structure:

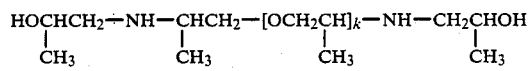

wherein k has a value of about 2.6;

(d) urea condensates of amine-terminated polypropylene glycols having the structure:

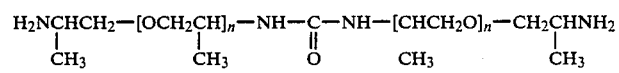

wherein n has a value of about 2.6; and (e) amine-terminated ethylene glycols having the structure:

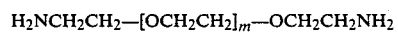

wherein m is an integer having a value of 1 to 3; and (f) amine-terminated polypropylene glycols having the structure:

wherein s has a value of about 1 to about 10, t has a value of about 2 to about 8, and R is hydrogen or methyl.

The preferred diamines are amine-terminated ethylene glycols having the structure:

$$H_2N-CH_2CH_2-[OCH_2CH_2]_m-OCH_2CH_2-NH_2$$

where m is as defined above.

This type of reaction may be illustrated as follows:

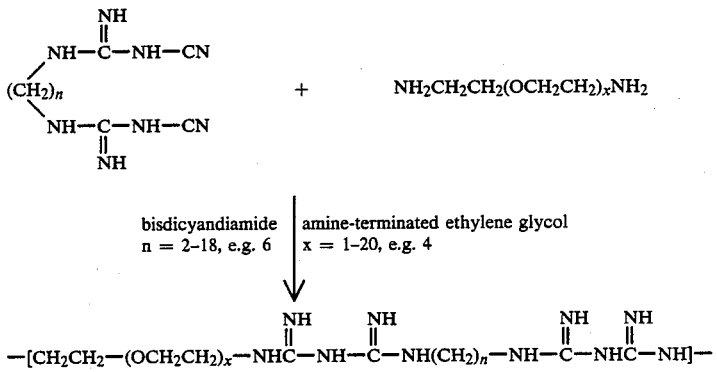

Alternatively the polyoxyalkylenediamines may be reacted with an inorganic salt of dicyanimide and a diamine or a diamine salt of dicyanimide as described in British patent No. 52,243.

The alternative type of reaction may be illustrated as follows:

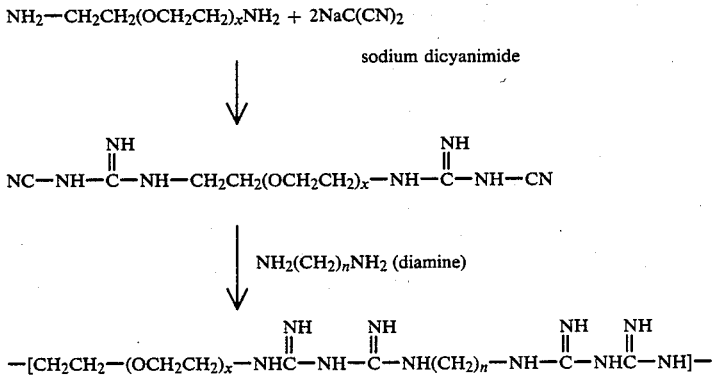

wherein n and x have the same range of values indicated above for the first type of reaction.

The invention is illustrated, but not limited, by the following examples in which all parts are by weight:

EXAMPLE 1

The compound known as 1,6-di($N^3$-cyano-$N^1$-guanidino) hexane was prepared in accordance with the description in example 1 of U.S. Pat. No. 4,537,746. The melting point of the compound was 206°–208° C. and its infrared spectrum was consistent with the desired structure.

EXAMPLE 2

A linear, polymeric biguanide was prepared from 12.5 g (0.05 m) of the biscyanoguanide of Example 1, 7.4 g (0.05 m) of triethyleneglycoldiamine and 10 cc (0.1 m) of conc. HCl which were heated to 145°–60°.C. for about 5 hours after driving off all the water. Upon cooling to room temperature, a light brown, glassy solid polymer was obtained in nearly a quantitative yield. The infrared spectrum of the product was consistent with the desired structure with no cyanide absorption being observed.

EXAMPLE 3

Example 2 was repeated using the biscyanoguanide of Example 1 and diethyleneglycoldiamine. The polymer of desired structure (as shown by its infrared spectrum) was obtained in nearly a quantitative yield.

EXAMPLE 4

Example 2 was repeated using the biscyanoguanide of Example 1 and tetraethylenglycoldiamine. Again, the polymer of desired structure (as shown by its infrared spectrum) was obtained in nearly a quantitative yield.

EXAMPLE 5

Example 2 was repeated using the biscyanoguanide of Example 1 and Jeffamine® D-2000, an amine-terminated polypropylene glycol having an approximate molecular weight of 2000 and the following structure:

wherein z has an average value of 33

The resultant polymeric biguanide had the desired structure as evidenced by its infrared spectrum and was obtained in nearly a quantitative yield.

EXAMPLE 6

Example 2 was repeated using the biscyanoguanide of Example 1 and Jeffamine ® ED-900, a polyether diamine having an approximate molecular weight of 900 and the following structure:

$H_2NCHCH_3CH_2-[OCHCH_3CH_2]_a-[OCH_2CH_2]_b-[OCH_2CHCH_3]_c-NH_2$ wherein b has an approximate value of 15.5 and a+c has an approximate value of 2.5.

The resultant polymeric biguanide had the desired structure as evidenced by its infrared spectrum and was obtained in a nearly quantitative yield.

EXAMPLE 7

Example 2 was repeated using the biscyanoguanide of Example 1 and Jeffamine ® DU-700, a urea condensate of an amine-terminated polypropylene glycol having an approximate molecular weight of 820 and the following structure:

$$\begin{array}{c} H_2NCHCH_3CH_2-[OCH_2CHCH_3]_n-NH \\ \diagdown \\ C=O \\ \diagup \\ H_2NCHCH_3CH_2-[OCH_2CHCH_3]_n-NH \end{array}$$

n = 5.6

The resultant polymeric biguanide had the desired structure as evidenced by its infrared spectrum and was obtained in a nearly quantitative yield.

EXAMPLE 8

The polymeric biguanides of Examples 2, 5, 6 and 7 were tested for their biocidal effectiveness against *Candida albicans* ATCC 10231 and *Staphylococcus epidermis* ATCC 17917. The time in minutes to kill 90% of the cells, i.e. the D-values, was less than 15 minutes for each biguanide (present in a concentration of 0.01 wt. %) in respect to each organism.

EXAMPLE 9

A fungistatic test was carried out using the polymeric biguanide of Example 4. A 0.02 wt. % aqueous solution of this biguanide (containing a few drops of a polyoxyethylene cetyl ether surfactant) was applied to the tiles which ere then allowed to air dry. A hard surface mildew fungistatic modified test, EPA Pesticide Registration Guidelines, subpart G using *Aspergillus niger* ATCC 16407 was carried out. Mildew growth on treated and untreated tiles was visually evaluated after 7 days of incubation. The test results indicated that 10 treated tiles showed no growth, while the 10 untreated tiles showed substantial growth after 7 days (the temperature and relative humidity were maintained at 25° C. and 95% during the test).

EXAMPLE 10

An excellent formulation for use in the sterilization of contact lenses, including hydrophilic gel lenses, may be prepared from the following ingredients:

| | |
|---|---|
| polymeric biguanide of Example 2 | 0.01 wt. % |
| sodium chloride | 0.50 wt. % |
| boric acid | 0.25 wt. % |
| sodium EDTA-adjusted to pH 7.0 | 0.05 wt. % |
| purified water Q. S. to make | 100.00 wt. % |

EXAMPLE 11

Following the procedure outlined in Example 2, the biscyanoguanide of Example 1 was reacted with Jeffamine ® EDR-148, a diamine with an approximate molecular weight of 148 and having the following structure:

$H_2N-CH_2CH_2-O-CH_2CH_2-O-CH_2CH_2-NH_2$

The resultant polymeric biguanide had the desired structure as evidenced by its infrared spectrum and was obtained in nearly quantitative yield.

EXAMPLE 12

Following the procedure outlined in Example 2, the biscyanoguanide of Example 1 was reacted with Jeffamine ® EDR-192, a diamine with an approximate molecular weight of 192 and having the following structure:

$NH_2CH_2CH_2(OCH_2CH_2)_2-OCH_2CH_2NH_2$

The resultant polymeric biguanide had the desired structure as evidenced by its infrared spectrum and was obtained in nearly quantitative yield.

EXAMPLE 13

Solutions were prepared with the polymeric biguanides of Examples 11 and 12. The D-values of these biguanides were assessed in respect to the organisms *S. marcescens* (organic load); *S. marcescens*; *C. albicans*; and *A. niger*. The D-values (approximate time in minutes for 90% reduction in viability at 26° C.) are listed for the Examples 11 and 12 biguanides together with several other commonly-used biocides in the table below.

| Organism | 11 | 12 | CXT | CX | TEACT | HP |
|---|---|---|---|---|---|---|
| S. marcescens (organic load) | 3.60 | 13.88 | ND | ND | ND | ND |
| S. marcescens | 3.41 | 9.00 | 0.22 | 24 | 24 | <25 |
| C. albicans | <0.25 | <1.0 | 15.0 | 5.0 | 76 | 50 |
| A. niger | 40 | 40 | 90 | 120 | 36 | 11 |

11 is the biguanide of Example 11 present in a concentration of 0.001 wt. %; 12 is the biguanide of Example 12 present in a concentration of 0.001 wt. %; CXT is a combination of thimerosal, 0.001 wt. %, chlorhexidine gluconate 0.005 wt. % and EDTA 0.1 wt. %; CX is chlorhexidine digluconate 0.005 wt. %; TEACT is alkyl triethanol ammonium chloride and thimerosal, 0.002 wt. %; HP is hydrogen peroxide, 3 wt. % (ND=not determined).

From the table above, it is readily apparent that the results achieved with the biguanides of the present invention are superior to those achieved with conventional biocides. In particular, it is to be noted that the polymeric biguanide of Example 11 showed a marked superiority to chlorhexidine, notwithstanding that it was present in the concentration of 1/5 of that of the chlorhexidine.

It is to be understood that the foregoing examples are illustrative only and that other means and techniques can be employed without departing from the true scope of the invention defined in the following claims.

I claim:

1. A linear, polymeric polyoxyalkylenediamine biguanide or water-soluble salt thereof which in the form of its free base comprises recurring units of the general formula

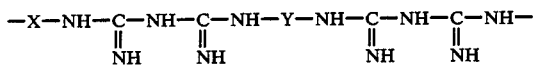

wherein X is a polyoxyalkylene radical and Y is a polymethylene radical of 2 to 18 carbon atoms or is the same as X.

2. The biguanide of claim 1 wherein Y is a polymethylene radical of 5 to 15 carbon atoms.

3. The biguanide of claim 1 wherein X is a polyoxyalkylene radical derived from the amines selected from the group consisting of:

(a) amine-terminated polypropylene glycols having the structure:

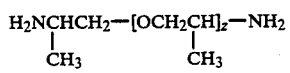

wherein z is an integer having a value of 2 to about 68;

(b) polyether diamines having the structure:

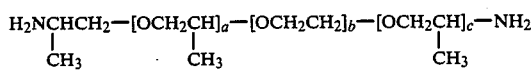

wherein b has a value of about 8.5 to about 131.5 and the value of a+c is about 2.5;

(c) bis-hydroxypropyl aminopolypropylene glycols having the structure:

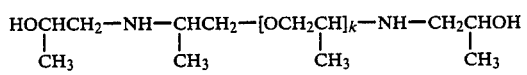

wherein k has a value of about 2.6;

(d) urea condensates of amine-terminated polypropylene glycols having the structure:

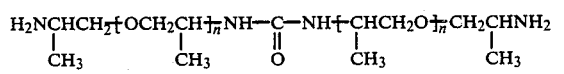

wherein n has a value of about 2.6; and (e) amine-terminated ethylene glycols having the structure:

wheren m is an integer having a value of 1 to 3; and (f) amine-terminated polypropylene glycols having the structure:

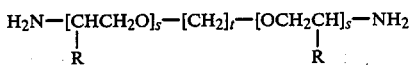

wherein s has a value of about 1 to about 10, t has a value of about 2 to about 8, and R is hydrogen or methyl.

4. The biguanide of claim 3 wherein the polyoxyalkylene radical is derived from amine-terminated ethylene glycols having the structure:

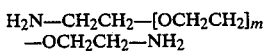

5. The biguanide of claim 1 wherein the water-soluble salt comprises a gluconate.

6. A fungicidal or bactericidal composition comprising, as an active ingredient, a linear polymeric polyoxyalkylene diamine biguanide or water-soluble salt thereof which in the form of its free base comprises recurring units of the general formula

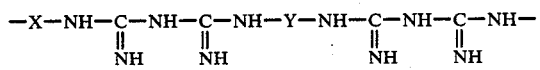

wherein X is a polyoxyalkylene radical and Y is a polymethylene radical of 2 to 18 carbon atoms or is the same as X, together with a carrier substance therefor.

7. The composition of claim 6 wherein Y is a polymethylene radical of 5 to 15 carbon atoms.

8. The composition of claim 6 wherein X is a polyoxyalkylene radical derived from the amines selected from the group consisting of:

(a) amine-terminated polypropylene glycols having the structure:

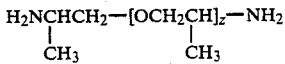

wherein z is an integer having a value of 2 to about 68;

(b) polyester diamines having the structure:

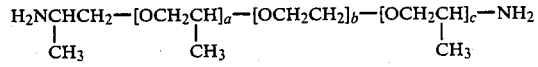

wherein b has a value of about 8.5 to about 131.5 and the value of a+c is about 2.5;

(c) bis-hydroxypropyl aminopolypropylene glocols having the structure:

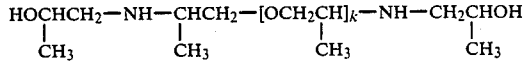

wherein k has a value of about 2.6;

(d) urea condensates of amine-terminated polypropylene glycols having the structure:

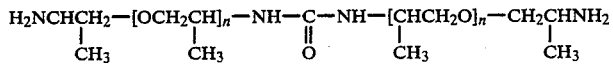

wherein n has a value of about 2.6;
(e) amine-terminated ethylene glycols having the structure:

$$H_2NCH_2CH_2-[OCH_2CH_2]_m-OCH_2CH_2NH_2$$

wherein m is an integer having a value of 1 to 3; and
(f) amine-terminated polypropylene glycols having the structure:

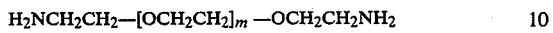

wherein s has a value of about 1 to about 10, t has a value of about 2 to about 8, and R is hydrogen or methyl.

9. The composition of claim 8 wherein the polyoxyalkylene radical is derived from amine-terminated ethylene glycols having the structure:

$$N_2N-CH_2CH_2[OCH_2CH_2]_m-OCH_2CH_2-NH_2$$

10. The biguanide of claim 6 wherein the water-soluble salt comprises a gluconate.

11. An ophthalmic composition comprising an aqueous solution of at least one opthalmically acceptable linear, polymeric polyoxyalkylenediamine biguanide or water-soluble salt thereof which in the form of its free base comprises recurring units of the general formula $$-X-NH-\underset{\underset{NH}{\|}}{C}-NH-\underset{\underset{NH}{\|}}{C}-NH-Y-NH-\underset{\underset{NH}{\|}}{C}-NH-\underset{\underset{NH}{\|}}{C}-NH-$$

wherein X is a polyoxyalkylene radical and Y is a polymethylene radical of 2 to 18 carbon atoms or is the same as X.

12. The composition of claim 11 wherein Y is a polymethylene radical of 5 to 15 carbon atoms.

13. The composition of claim 11 wherein X is a polyoxyalkylene radical derived from the amines selected from the group consisting of:
(a) amine-terminated polypropylene glycols having the structure:

wherein z is an integer having a value of 2 to about 68;
(b) polyether diamines having the structure:

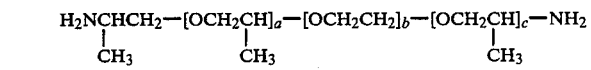

wherein b has a value of about 8.5 to about 131.5 and the value of a+c is about 2.5;
(c) bis-hydroxypropyl aminopolypropylene glycols having the structure:

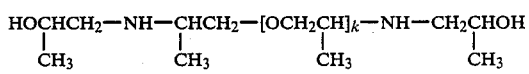

wherein k has a value of about 2.6;
(d) urea condensates of amine-terminated polypropylene glycols having the structure

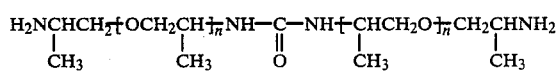

wherein n has a value of about 2.6;
(e) amine-terminated ethylene glycols having the structure:

$$H_2NCH_2CH_2-[OCH_2CH_2]_m-OCH_2CH\ 2NH_2$$

wherein m is an integer having a value of 1 to 3; and
(f) amine-terminated polypropylene glycols having the structure:

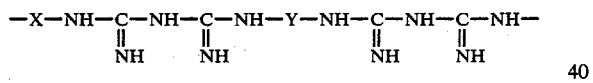

wherein s has a value of about 1 to about 10, t has a value of about 2 to about 8, and R is hydrogen or methyl.

14. The composition of claim 13 wherein the polyoxyalkylene radical is derived from amine-terminated ethylene glycols having the structure:

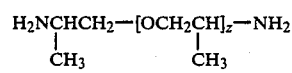

15. The composition of claim 11 wherein the water-soluble salt comprises a gluconate.

16. The composition of claim 11 wherein the biguanide or its salt is present in an amount of from 0.001 to 0.1% by weight, based on the weight of the total composition.

* * * * *